United States Patent [19]

Reekie

[11] Patent Number: 4,526,045
[45] Date of Patent: Jul. 2, 1985

[54] SAMPLING SYSTEM

[75] Inventor: John Reekie, Warrington, England

[73] Assignee: British Nuclear Fuels Limited, Warrington, England

[21] Appl. No.: 486,212

[22] Filed: Apr. 18, 1983

[30] Foreign Application Priority Data

May 5, 1982 [GB] United Kingdom ............... 8212943

[51] Int. Cl.[3] .............................................. G01N 1/10
[52] U.S. Cl. ............... 73/864.31; 73/864.52; 376/245
[58] Field of Search ............... 73/863, 864.31, 864.52; 422/63, 65; 376/245

[56] References Cited

U.S. PATENT DOCUMENTS

| 2,968,183 | 1/1961 | Hannaford | 73/864.31 |
| 3,383,923 | 5/1968 | Conche et al. | 73/864.31 |
| 3,907,231 | 9/1975 | Kreiner | 406/111 |
| 4,160,382 | 7/1979 | Finsterwalder . | |
| 4,395,164 | 7/1983 | Beltrop | 406/112 |

FOREIGN PATENT DOCUMENTS 1111114  4/1968  United Kingdom .

Primary Examiner—S. Clement Swisher
Attorney, Agent, or Firm—William R. Hinds

[57] ABSTRACT

A sampling system in which carriers (1) containing sample bottles (4) are transported by pneumatic conveyor means (3) between an examination station, for example a laboratory, and a selected sampling station at a plant. On arrival at a sampling station (2) a bottle (4) is moved through a predetermined sequence of movements by a transfer arm (5) to cause the bottle to be removed from its carrier and placed over a sample dispenser (7) to introduce sample into the bottle. The bottle containing sample is then returned to the carrier for return to the examination station.

9 Claims, 10 Drawing Figures

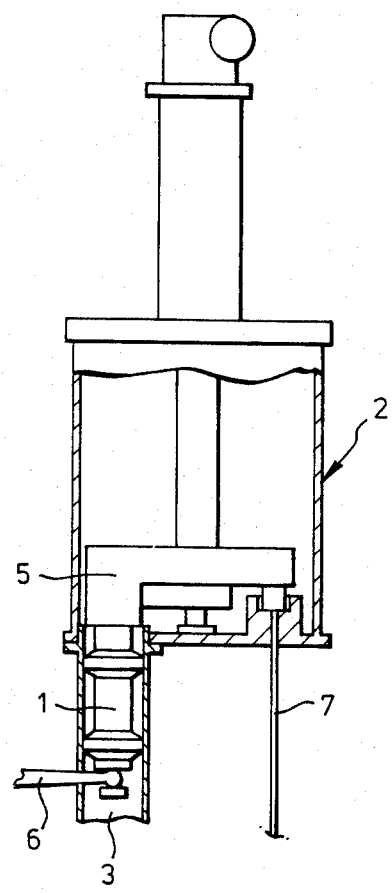
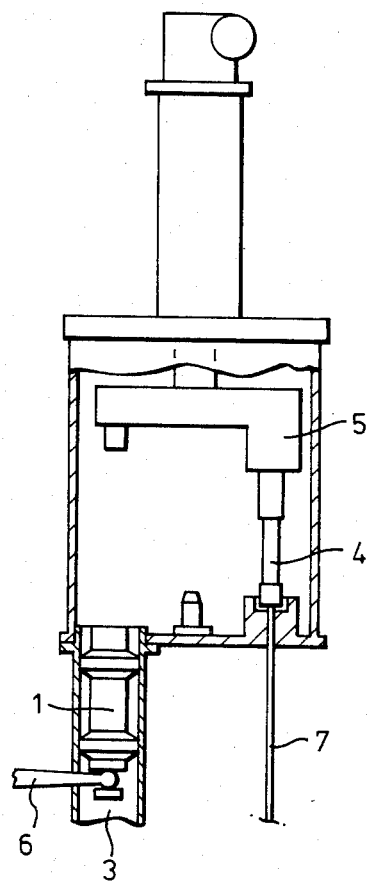
Fig.1.
Fig.2.

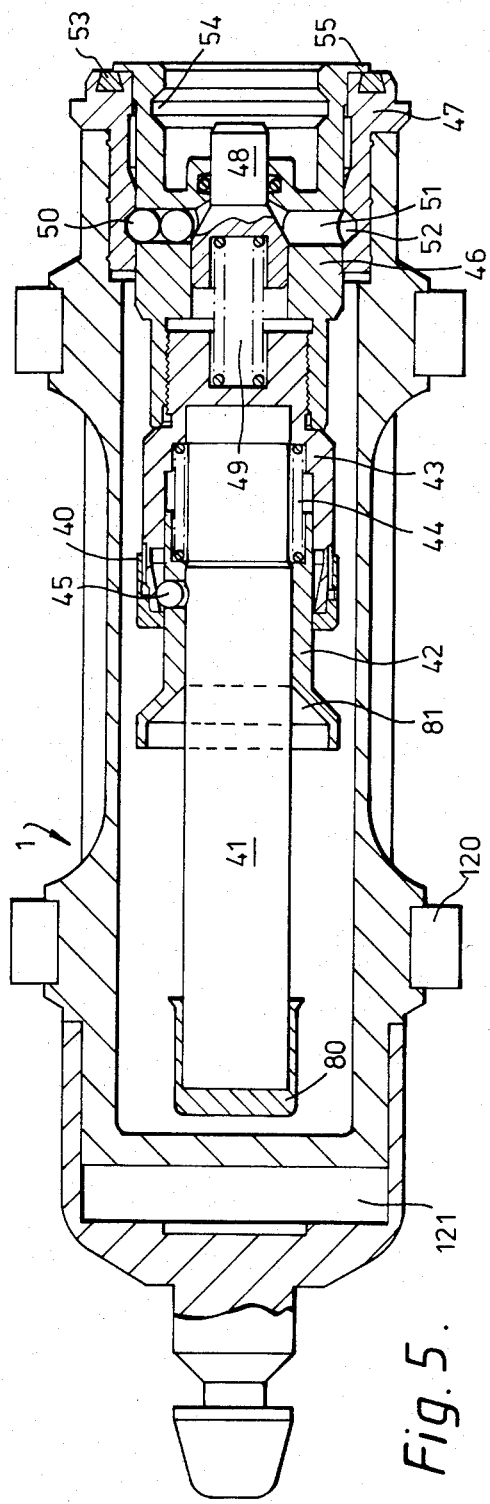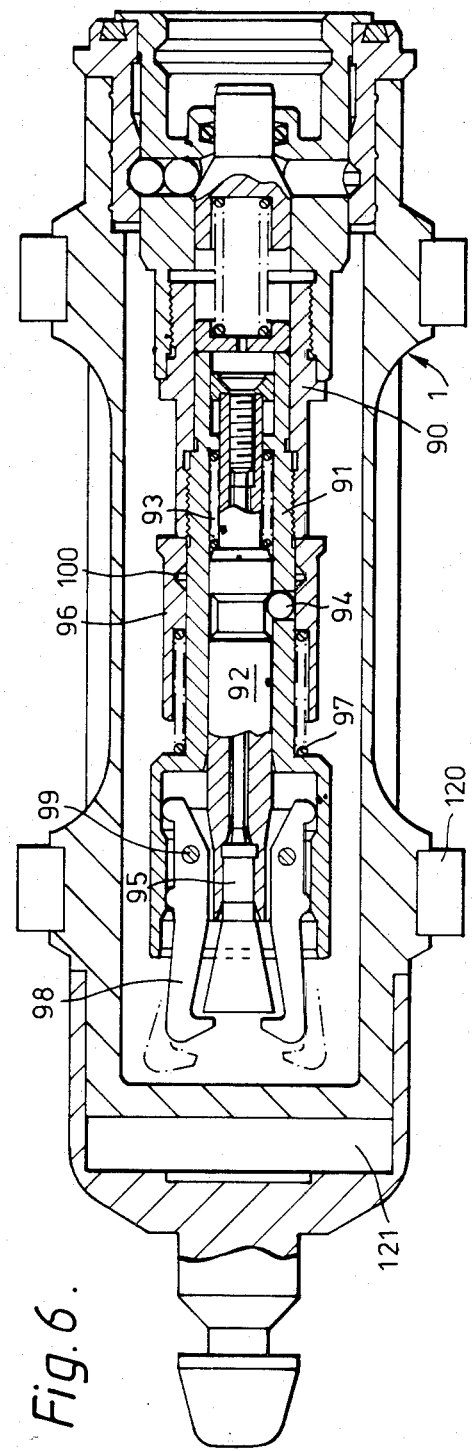
Fig. 5.
Fig. 6.

SAMPLING SYSTEM

The present invention concerns a system for obtaining samples.

BACKGROUND OF THE INVENTION

In the nuclear industry it is frequently required to obtain samples of a radioactive liquid, for example, in a plant for the reprocessing of irradiated nuclear fuel. Sampling can be carried out by an operator who enters an active area to obtain a sample. The sample can then be conveyed to an examination station, such as a laboratory, within a shielded flask. It is now proposed to dispense with the services of an operator for collecting samples and to provide alternative means for the transport of the samples.

FEATURES AND ASPECTS OF THE INVENTION

According to the present invention a sampling system comprises an examination station, a sampling station, pneumatic conveyor means between the stations, carrier means for transporting sample bottles along the conveyor means between the stations, means at the sampling station to receive a carrier, remove the sample bottle from the carrier deliver the bottle to a sample dispenser to introduce sample into the bottle and thereafter to return the bottle to the carrier for return to the examination station.

Conveniently, the system includes means for automatically and remotely replacing the sample dispenser in the event of wear and damage. When the sample is a liquid the dispenser can comprise a needle to introduce the sample into the bottle. The system can be installed at a plant site with the examination station being a central laboratory and the sampling station or a number of sampling stations being at a location or locations on the plant site remote from the laboratory.

DESCRIPTION OF THE DRAWINGS

The invention will be described further, by way of example, with reference to the accompanying drawings; in which:

FIG. 1 is a diagrammatic illustration showing a sampling station with a carrier docked at the sampling station and prior to the withdrawal of a bottle from the carrier into the sampling station;

FIG. 2 is a diagrammatic illustration showing the carrier docked in position as in FIG. 1 and with the bottle removed from the carrier and indexed to a needle to receive sample;

FIG. 5 is a sectional elevation of the carrier containing the bottle;

FIG. 6 shows a needle withdrawal unit;

DESCRIPTION OF THE PREFERRED EMBODIMENTS

Figure 3:
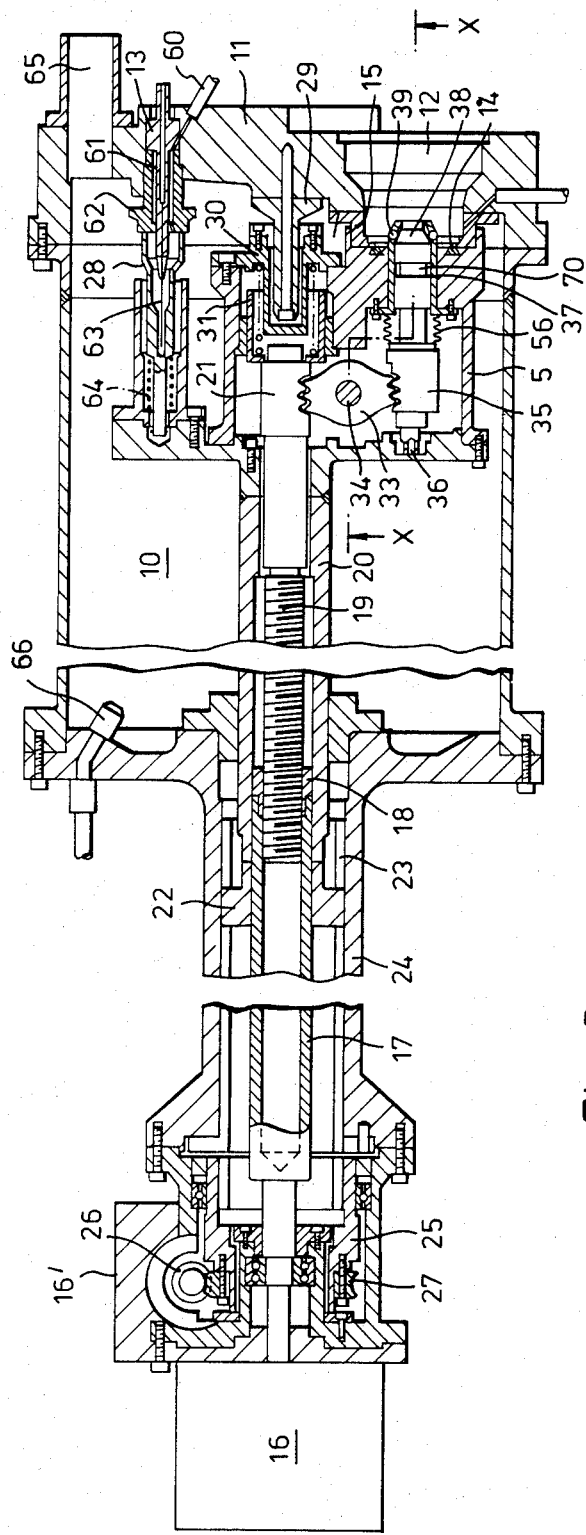
FIG. 3 is a detailed sectional elevation of the sampling station.
Figure 4:
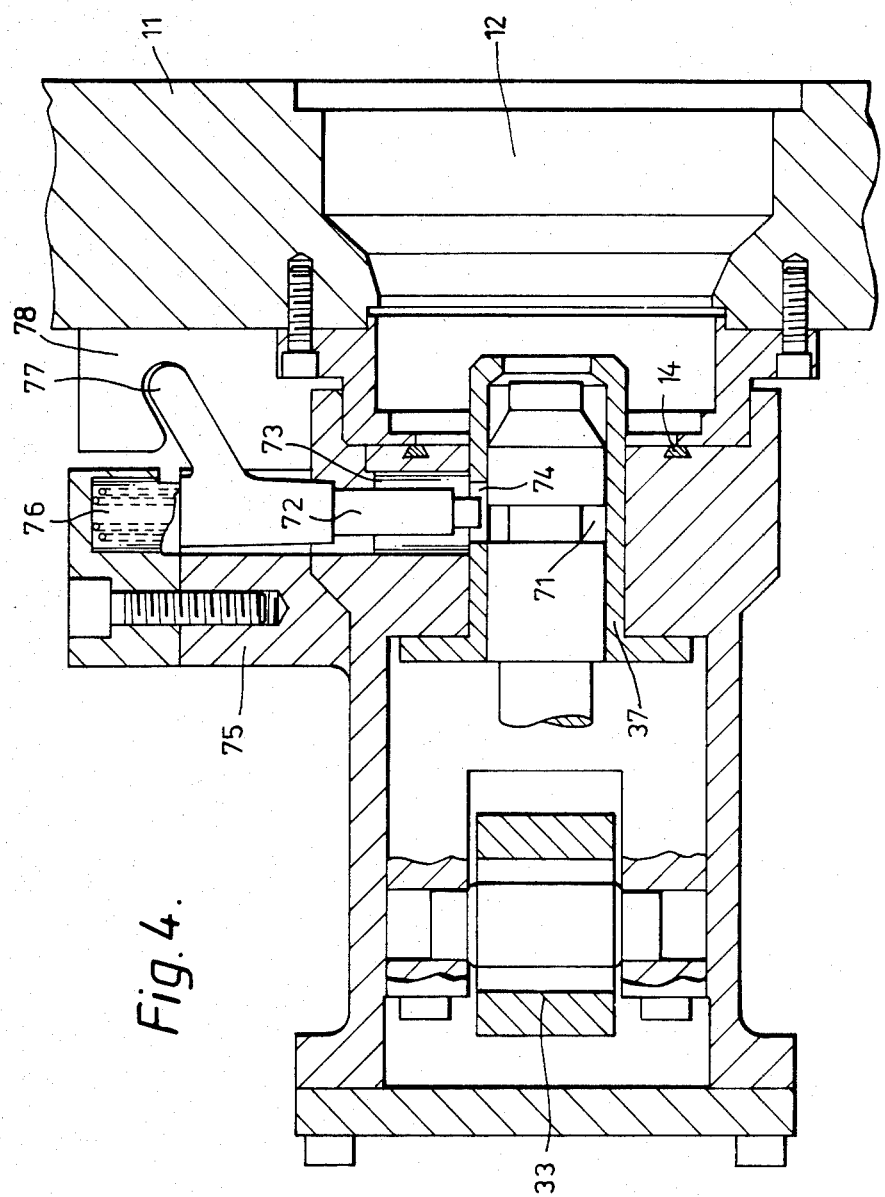
FIG. 4 is a section (not to scale) on line X—X in FIG. 3.

In FIG. 1, a carrier 1 containing a bottle is shown docked at a sampling station 2 after travel along a duct 3 from an examination station. The carrier is propelled pneumatically along the duct 3, preferably by creating a pressure drop (suction) ahead of the carrier in the direction of travel. At the sampling station 2 the carrier 1 is releasably held by a clamp 6 in its docked position to cooperate with a transfer arm 5 which latter can disengage the bottle 4 from the carrier, lift the bottle axially out of the carrier, index the bottle above a needle 7 and lower the bottle on to the needle, (as depicted in FIG. 2). After the injection of a sample into the bottle the transfer arm performs a reverse sequence of movements to return the bottle to the carrier. The transport system between the stations can include diverters, exhausters, control valves and monitoring and control apparatus.

The sampling station 2 comprises a chamber 10 housing the transfer arm 5. An end of the chamber is closed by a base plate 11 having a docking port 12 to receive the carrier 1. At least one needle carrier 13 extends through the base plate and into the chamber 10. In the absence of a carrier 1 the port 12 is sealingly closed by the transfer arm 5. A sealing ring 14 in the arm engages the rim of a sealing ring 15 at the port, the sealing ring 14 partly projecting inwardly beyond the rim of the ring 15 for a purpose to be described. The transfer arm 5 is capable of axial and rotational movement by means of two stepping motors. A first stepping motor 16 moves the arm 5 axially by means of a hollow drive shaft 17 terminating in a nut 18 which engages a threaded spindle 19. The spindle is located within an axial sleeve 20 secured to the transfer arm and rotation of the hollow drive shaft 17 by the first stepping motor displaces the spindle axially in direction away from the base plate 11. An enlarged end portion 21 of the spindle engages the transfer arm to displace the latter axially within the chamber 10 and away from the base plate 11. The end of the sleeve 20 remote from the transfer arm is provided with keys 22 which cooperate with keyways in a cylindrical liner 23 secured within an extension housing 24. The keys and keyways cooperate to permit axial displacement of the transfer arm and to prevent rotational movement of the arm until the keyed end of the sleeve 20 clears the end of the liner 23. In this fully withdrawn position the keyed end of the sleeve enters and engages a wormwheel housing 25. A second stepping motor 16' rotates the housing 25 through a worm 26 and wormwheel 27 mounted on the housing and this rotational drive is transmitted by the sleeve 20 to rotate the transfer arm 5. The arm is rotated through an arc to bring a bottle carried thereon directly above a needle mounted in the needle carrier 13. Thereafter the rotation is stopped and the transfer arm is displaced axially to lower the bottle on to the needle by operating the first stepping motor in a reverse direction.

In FIG. 3 the transfer arm 5 is in its lowered position to sealingly close the docking port 12 by means of the cooperating sealing rings 14 and 15. A shroud 28 protects the needle. The spindle 19 is located in line with a location spigot 29 mounted centrally on the base plate 11. A cup 30 on the transfer arm engages the spigot 29 and a cylindrical housing 31 is arranged about the cup and is urged by a spring 32 against the enlarged end 21 of the spindle. With the transfer arm lowered to abut the base 11, the end 21 of the spindle is spaced from the cup 30 to form a lost motion drive connection. Continued downward movement of the spindle is possible until the end of the spindle abuts against the end of the cup. This continued movement causes a gear 33 journalled in the transfer arm to pivot about its axis 34 to axially displace a bobbin 36 against action of a compression spring 36. The bobbin is slidable in a sleeve 37 fixed in the transfer arm and the movement of the bobbin relative to the sleeve causes a mitred end 38 of the bobbin to withdraw into the sleeve. The withdrawal of the mitred end of the bobbin frees balls 39 at the end of the sleeve 37, which balls in their outward position lock the bobbin to a lid of a bottle carrier. Thus this final movement of the spindle 19 to effect displacement of the bobbin 35 allows the transfer arm to delatch itself from the carrier lid. Conversely, on lifting the spindle 19 the first initial movement before the enlarged part of spindle engages the transfer arm depresses the bobbin 35 to cause the outward movement of the balls 39 into a locking position.

The carrier 1, containing a bottle holder 40 and a bottle 41 is seen in FIG. 5. The holder is formed from two telescopic parts 42 and 43 which are normally maintained extended by a spring 44. In this extended position balls 45 in the part 42 are urged radially inwards by an inclined surface on the part 43 to engage recesses in the bottle 41 to thereby latch the bottle to the holder. On contracting the holder against the action of the spring 44 the balls 45 can move along the inclined face on the part 43 to withdraw radially outwards and thereby delatch the bottle. The part 43 of the holder is screwed to carrier lid 46 which cooperates with an insert 47 fixedly secured in the end of the carrier. The lid 46 carries a plunger 48 which is urged by a spring 49 in a direction towards the open end of the lid and away from the bottle holder. The portion of the plunger adjacent the bottle holder is of an enlarged diameter. The resulting tapered intermediate portion of the plunger 48 cooperates with balls 50 located in radial bores 51 in the lid. With the plunger urged by the spring 49 away from the bottle holder the balls 50 are retained by the tapered portion of the plunger to project outwardly beyond the surface of the lid and engage a recess 52 in the insert 47 at the end of the carrier. In this position the lid, and hence the bottle holder and bottle, are latched or locked in position within the carrier. A sealing ring 53 is recessed in the rim of the insert 47 at the end of the carrier. This end of the carrier is the leading end when approaching the docking port 12 along the pneumatic transfer duct 3. When engaging in the docking port 12 the end of the lid 46 receives the end of the sleeve 37 about the bobbin 35 (FIG. 3), the bobbin itself being in a withdrawn position whereby the balls 39 are recessed within the sleeve 37. To lock the lid to the transfer arm the bobbin is advanced as before described such that the balls 39 are urged outwards and are held in engagement with a groove 54 in the lid 46. At the same time the end of the bobbin 35 abuts against the end of the plunger 48 to urge the latter against the action of the spring 49 to thereby release the balls 50 from the recess 52 in the insert 47. Hence the bottle 41 carried by the holder 40 is delatched from the carrier and is latched to the transfer arm.

The carrier during its stay at the docking port 12 is urged into sealing engagement with the port by means of a clamp bearing against the closed end of the carrier. It will be noticed that the lid has a peripheral lip 55 which engages the rim of the insert 47 adjacent the seal 53. When initially positioned in the docking port this lip 55 bears against the free exposed portion of the sealing ring 14 in the transfer arm and the sealing ring 53 in the insert bears against the rim of the sealing ring 15 at the docking port. The sealing rings function to maintain a seal at the docking port at all times both in the absence of and presence of the carrier and bottle.

A flexible resilient bellows 56 (FIG. 3) is arranged about a portion of the bobbin 35 and is anchored to the sleeve 37. The bellows 56 functions to isolate the interior of the transfer arm 5 from the portion of the bobbin slidable within the sleeve.

A water wash facility can be provided for the needle. With reference to FIG. 3, a connection 60 in the base plate 11 communicates with an annular passageway 61 formed between the needle carrier 13 and a surrounding plug 62. The passageway 61 opens into a compartment formed about the needle 63 when the shroud 28 is lowered about the needle. The shroud is urged into contact with the plug by a spring 64. On lifting shroud off the plug water can escape through a drain outlet 65 in the base plate 11.

The interior of the chamber 10 can also be spray cleaned with water through jets 66 located in the end wall of the chamber opposite the base plate 11.

The bobbin 35 is formed with a reduced diameter portion 70 within the sleeve providing a peripheral groove 71 adapted to receive the end of a plunger 72 slidable in a transverse bore 73 in the transfer arm and an opening 74 in the sleeve 37. The opposite end of the plunger 72 engages a recess in a guide block 75 which is secured to or forms a part of the transfer arm. A bore in this opposite end of the plunger 72 receives a spring 76 which acts to urge the plunger in a direction to engage the bobbin. The plunger in addition has an inclined arm or spigot 77 which cooperates with a similarly inclined recess in a block 78 secured to the base plate 11. The plunger 72 cooperates with the groove 71 in the bobbin to form an interlock and functions as follows:

Normally, with the transfer arm at the docking port, the inclined extension arm 77 will cooperate with the recess in the block 78 to hold the plunger 72 in a withdrawn position out of engagement with the bobbin. The bobbin is thereby free to move, as a result of the rocking of the gear 33, to release or engage the lid and bottle holder. In the engaged position the opening 74 in the bobbin sleeve is in alignment with the groove 71. When the transfer arm is lifted clear of the base plate 11 to move the bottle from its carrier the arm 77 on the plunger 72 moves out of its recess in the block 78 and the plunger can move axially under the influence of the spring 76 to engage in the groove 71 and hence lock the bobbin against axial movement. Consequently the lid and bottle holder are securely locked to the bobbin and remain so until they are returned to the docking port at the end of a sampling operation. On return, the inclined extension arm 77 on the plunger 72 enters the groove in the block 78 and in so doing causes the plunger to be withdrawn axially away from the groove 71 in the bobbin, thus releasing the bobbin for axial movement.

The bottle 41 comprises a cylindrical vessel closed at one end and having a removable closure cap 80 at its opposite end. The closed end of the bottle is inserted into the bottle holder 40 and the opposite end projects beyond the holder so that the closure cap 80 can engage and be pierced by a needle. The cap is formed from a material which is self-sealing after withdrawal from the needle. The cap can be silicone rubber. Prior to dispatch the bottle can be evacuated such that sample is sucked into the bottle on piercing of the cap by the needle. The holder 40 has a flared end 81 to assist in the location or insertion of the bottle.

It is anticipated that the most common maintenance operation during operation will involve sample needle replacement. This can be performed automatically and remotely by means of the pneumatic system and transfer arm. A needle insertion unit and a needle withdrawal unit can be arranged within the carrier for transport to and from the assembly.

The needle withdrawal unit (FIG. 6) is attached to the lid of the carrier and replaces the bottle holder. It is releasably secured in the carrier in an identical manner to the bottle holder and is operatively engaged by the bobbin as before. The unit is attached to the lid 46 by an adaptor 90 and a cam tube 91 is in turn secured to the adaptor by screw thread connections. A plunger 92 is slidable within the bore of the cam tube, the plunger being urged in a direction away from the adaptor by a spring 93. A reduced diameter portion of the plunger intermediate its ends cooperates with latching balls 94 which are located in apertures in the tube 91. In the illustrated position in which the withdrawal unit is engaged about the end of a needle 95, the balls 94 extend into the reduced diameter portion of the plunger and are held in position by means of a sleeve 96 slidable on the exterior of the tube 91. The sleeve 96 is urged by a spring 97 in a direction towards the adaptor 90. At its end remote from the adaptor the cam tube terminates in an enlarged diameter portion to receive claw pieces 98. The claw pieces 98 pivot on pins 99 located on brackets at the end of the plunger 92. The interior surface of the enlarged diameter portion is profiled to form a cam surface which cooperates with the claw pieces to cause the claw pieces to pivot about their pins on relative movement of the claw pieces and the cam surface.

In operation the withdrawal unit is lowered by the transfer arm on to a needle carried in the needle carrier 13.

The needle tip enters the bore in the plunger 92. Initially, the claw pieces 98 are in their open position as shown in dotted outline in FIG. 6 and the reduced diameter portion of the plunger is out of engagement with the balls 94 which are moved radially outwardly from the shown position to engage recesses 100 in the sleeve 96. When needle tip enters the bore in the plunger and as the needle is fixed on its carrier against axial movement downwards, further movement of the unit causes the plunger 92 to move into the position shown and to engage the claw pieces about the end of the needle. When the plunger moves up into the tube, the claw pieces are caused to pivot in moving across the cam surfaces. When the reduced diameter portion of the plunger arrives at the balls 94, the balls are urged inwards by the spring-loaded sleeve 96 to thereby lock the plunger and hence the claw pieces 98. The needle can then be withdrawn with the unit and returned to carrier.

Figure 7:
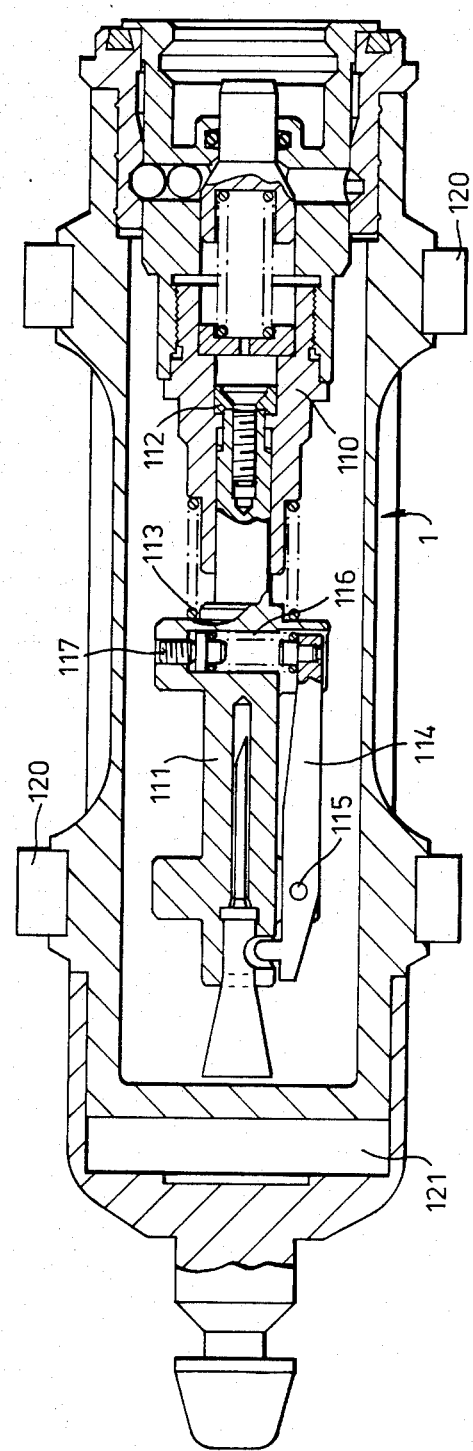
FIG. 7 shows a needle insertion unit.

The needle insertion unit shown in FIG. 7 comprises an adaptor 110 for connection to the lid of the carrier 1. This adaptor 110 is similar to the adaptor 90 of the needle withdrawal unit. The adaptor 110 carries a needle holder 111 which is slidable in the bore in the adaptor. The end of the holder within the bore in the adaptor passes through a reduced diameter portion of the bore and is retained from dropping out by a cap 112 secured to the end of the holder by a screw. A spring 113 about the end of the adaptor engages the holder and urges the latter in a direction away from the adaptor such that the cap abuts against the reduced diameter portion which forms a stop. The holder 111 carries a pawl 114 journalled to pivot about a pin 115 carried by lugs on the exterior of the holder. The pawl is urged to pivot in a clockwise direction as shown in drawing and to engage the needle by means of a spring 116 acting on the end of the pawl. The spring tension is adjustable by a set screw 117. The end of pawl engageable with the needle has a rounded projection which is biassed by the spring 116 to retain the needle within the holder. When lowering into position on to the needle carrier the needle abuts against the needle carrier and any further continued downward movement of the unit causes the holder 111 to move into the adaptor 110 against action of the spring 113. With the needle positioned on its carrier the unit is withdrawn by lifting off the needle. The spring 116 is adjusted such that the pawl exerts sufficient pressure on the needle to carry and locate the needle on its carrier but allows the unit to be withdrawn to leave the needle in place on its carrier.

As shown in the drawings the carrier 1 is provided with rings 120 which provide sliding contact with the interior of the duct 3. Further the carrier 1 contains a permanent magnet 121 which serves to actuate electromagnetic switches positioned at intervals along the length of the duct 3 to thereby indicate the passage of the carrier along the duct.

Conveniently, a plurality of needles can be provided at the sampling station. For example three needle positions can be provided and the stepping motor 16' can be programmed to index a bottle through an appropriate arc to bring the bottle in line with the required needle.

Figure 8A:
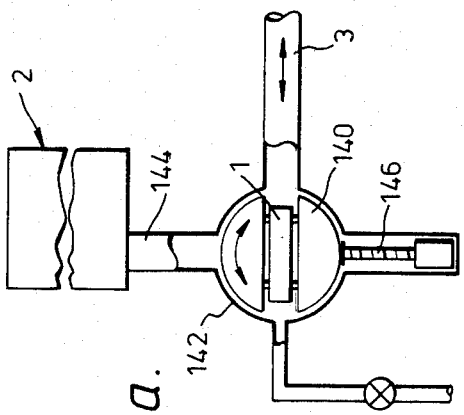
FIGS. 8 and 8a are diagrammatic examples of arrangements for a smooth docking of a carrier at the sampling station.
Figure 8:
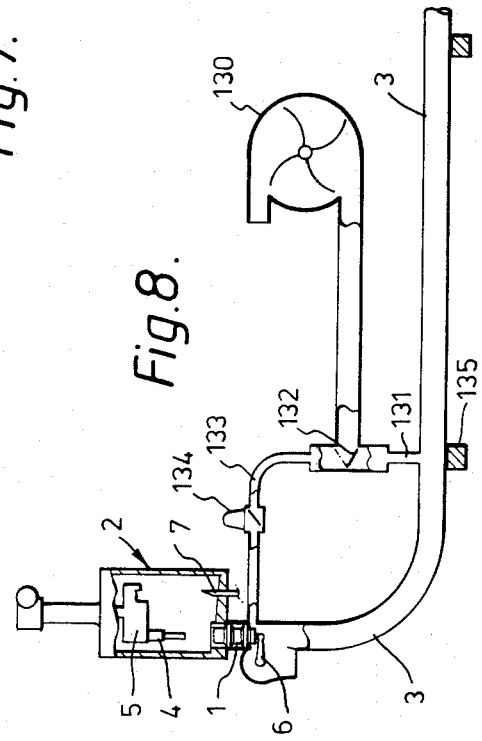

FIG. 8 shows one possible arrangement for a smooth, bumpless arrival of the carrier at the sampling station. Carrier 1 is drawn along conduit 3 by exhauster (suction pump) 130 which is connected to the conduit 3 at a junction 131 spaced from the sampling station by a two-wave valve 132. During travel along the conduit 3 to the junction the valve 131 is in the dotted position whereby to connect the exhauster to the conduit 3 and to isolate the exhauster from a narrow bore conduit 133 containing a motorised valve 134 and communicating with the conduit 3 in the region of the clamp 6 adjacent the sampling station.

With the valve 132 in its dotted position the carrier is drawn along the conduit 3 to the junction 131 and halts at the junction as the exhauster 130 is isolated from the length of conduit 3 between the junction 131 and the sampling station 2. The presence of the carrier at the junction is detected by electro-magnetic switch 135 (actuated by the magnet on the carrier) and the signal so generated causes change-over valve 132 to assume its full-line position shown in FIG. 8 and the motorised valve 134 in conduit 133 to open. As a result suction is applied to the conduit 3 ahead of the carrier to draw the carrier to the junction of the conduit 133 with the conduit 3. As the conduit 133 is of narrow bore the speed of travel of the carrier along the length of conduit 3 between the junctions is considerably less than the previous speed of travel along the conduit 3 to the junction 131. A further electromagnetic switch at the junction of the conduits 3 and 133 detects the arrival of the carrier and initiates sequentially the actuation of clamp 6, which latter can be coupled to a pneumatic piston and cylinder and to switch off exhauster 130. The clamp operates to contact the end of the carrier remote from the sampling station and to urge the carrier into firm docking engagement at the sampling station. Sensing means at the sampling station detect the arrival and docking of the carrier and initiate a pre-programmed sequence of operations to cause the transfer arm 5 to remove the bottle 4 from the carrier and transfer the bottle to a needle 7 to obtain a sample. The bottle can be located on the needle for a pre-set time after which the transfer arm returns the bottle, now containing sample, to the carrier. Completion of this controlled sequence of operations initiates a further stage in the programme to withdraw the carrier containing the bottle along the conduit 3 to the laboratory. The carrier is again propelled along the conduit by suction created by a further exhauster at the laboratory end of the conduit. The conduit at the laboratory can be arranged, in a manner similar to that described at the sampling station, to achieve a smooth, bumpless docking at the laboratory.

FIG. 8a shows in diagram form an alternative arrangement for docking the carrier at the sampling station. As before, the carrier 1 is drawn along conduit 3 by an exhauster to enter a turntable 140 located within a housing 142. The arrival of the carrier initiates rotation of the turntable 140 to align the carrier with an exit tube 144 leading to the docking port at the sampling station 2. Thereafter the carrier is lifted vertically out of the turntable and to the docking port by a screw jack or ram 146 which holds the carrier in position at the docking port. The return operation is the reverse of the above, that is, the ram is lowered to return the carrier to the turntable and the turntable then rotates to align the carrier with the conduit 3. The above operations are performed automatically and in sequence.

The examination station can be a central laboratory to despatch and receive bottles and a number of different sampling stations can be linked to the examination station by a pneumatic conveyor system. In such a system the carriers containing the bottles are propelled along ducts preferably by suction, and the system can include known diverters, control valves, monitoring and control equipment. The ducts can be provided with radiation shielding at lengths which are exposed or accessible to plant personnel.

Figure 9:
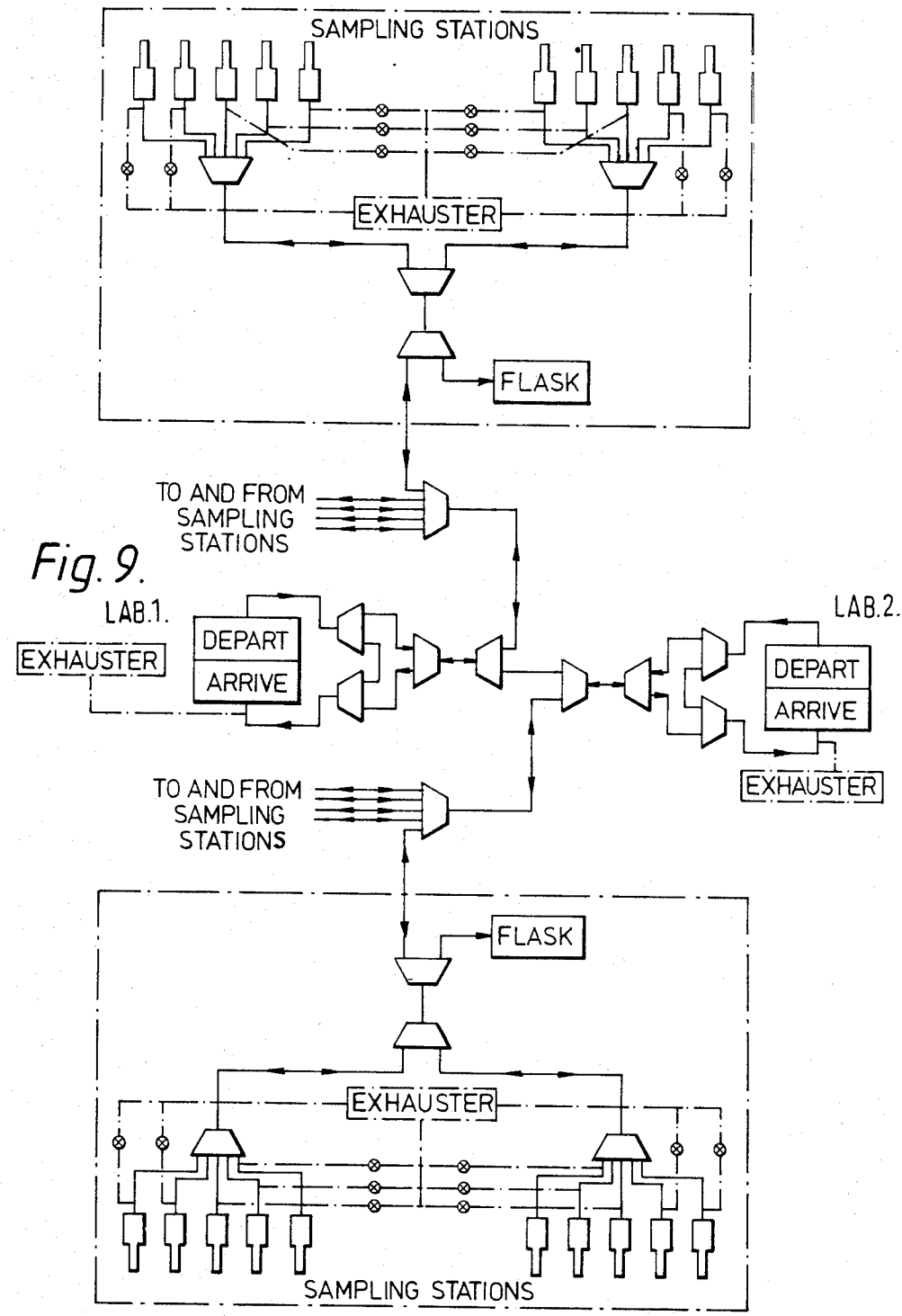
FIG. 9 is a line diagram of an example of a sampling system.

As an example only, FIG. 9 depicts a sampling system at an industrial plant for the reprocessing of irradiated nuclear fuel elements. In this example the examination station comprises two laboratories, for example, LAB 1 for material of low specific radioactivity and LAB 2 for material of high specific radioactivity. LAB 1 and LAB 2 are each capable of communicating with a plurality of sampling stations. The number of laboratories and sampling stations can be chosen to suit plant requirements and in FIG. 9, and purely as an example, each laboratory can communicate with five groups of ten sampling stations with each group being, for example, at a different location or building on the plant site. The paths of travel between the laboratories and the sampling stations are provided by the conduits for the carriers and by the diverters which are selectively and remotely operable to direct a carrier along a desired route. Exhausters (suction pumps) are provided at the sampling stations and the laboratories to draw the carriers along the conduits and electromagnetic switches are provided along the paths of travel to provide an indication of the passage of the carriers. The system can be controlled and programmed from a control position at each laboratory such that a required route can be selected and set up by an operator. A posting facility for transferring a carrier or carriers to a flask can be provided at each group of sampling stations. Such a posting facility can be used in situations where it is not convenient or desirable to return the carrier or carriers to the laboratories by way of the pneumatic conveyor system.

It will be appreciated that the invention is not confined to use in obtaining samples of radioactive liquid in a nuclear fuel reprocessing plant. The invention is applicable in other situations in which it is desirable to obtain samples automatically at locations remote from an examination station.

I claim:

1. A sampling system comprising an examination station, a sampling station, pneumatic conveyor means between the stations, carriers for transport along the conveyor means between the stations, sample bottles carried by the carriers and transfer means at the sampling station including a transfer arm operable to (a) cooperate with a carrier, (b) remove the bottle from the carrier (c) deliver the bottle to a sample dispenser to introduce sample into the bottle and (d) return the bottle containing sample to the carrier for return to the examination station.

2. A sampling system according to claim 1 in which the sampling station comprises a chamber housing the transfer arm with a docking port for a carrier in an end wall of the chamber.

3. A sampling system according to claim 2 including cooperable sealing means between the transfer arm and the docking port.

4. A sampling system according to claim 2 including a lost-motion drive connection to effect latching and delatching between the transfer arm and a carrier when the transfer arm abuts against the end wall of the chamber.

5. A sampling system according to claim 4 including a releasable lid on the carrier and interlock means operable to lock the lid to the transfer arm when the transfer arm is moved from the docking port.

6. A sampling system according to claim 2 in which the sample dispenser comprises a replaceable needle, a needle carrier for the needle extending through the end wall of the chamber.

7. A sampling system according to claim 6 including a needle withdrawal unit and a needle insertion unit each cooperable with the transfer arm for moving a needle between the needle carrier and a carrier at the docking port.

8. A sampling system according to claim 1 including drive means for effecting separate axial and rotational movements of the transfer arm.

9. A sampling system according to claim 1 including at least one examination station and a plurality of sampling stations.

* * * * *